(12) United States Patent
Kaminaga

(10) Patent No.: US 10,409,050 B2
(45) Date of Patent: Sep. 10, 2019

(54) ADAPTOR FOR ATTACHING PORTABLE TERMINAL

(71) Applicant: MICROSCOPE NETWORK CO., LTD., Kawaguchi-shi, Saitama (JP)

(72) Inventor: Ryohei Kaminaga, Kawaguchi (JP)

(73) Assignee: MICROSCOPE NETWORK CO., LTD., Kawaguchi-Shi, Saitama (JP)

( * ) Notice: Subject to any disclaimer, the term of this patent is extended or adjusted under 35 U.S.C. 154(b) by 0 days.

(21) Appl. No.: 15/547,241

(22) PCT Filed: Dec. 28, 2015

(86) PCT No.: PCT/JP2015/086473
§ 371 (c)(1),
(2) Date: Jul. 28, 2017

(87) PCT Pub. No.: WO2017/046973
PCT Pub. Date: Mar. 23, 2017

(65) Prior Publication Data
US 2018/0180866 A1    Jun. 28, 2018

(30) Foreign Application Priority Data
Sep. 15, 2015    (JP) ................................ 2015-181428

(51) Int. Cl.
*G02B 21/36*    (2006.01)
*H04M 1/21*    (2006.01)
(Continued)

(52) U.S. Cl.
CPC ......... *G02B 21/362* (2013.01); *G02B 21/361* (2013.01); *G03B 17/566* (2013.01);
(Continued)

(58) Field of Classification Search
CPC .. G02B 21/362; G02B 21/248; G02B 21/361; G02B 21/24; H04M 1/06; H04M 1/21;
(Continued)

(56) References Cited

U.S. PATENT DOCUMENTS

| | | |
|---|---|---|
| 2010/0142036 A1 | 6/2010 | Sterns et al. |
| 2012/0262540 A1 | 10/2012 | Rondinelli et al. |
| 2013/0016963 A1* | 1/2013 | Miller .................. G02B 21/362 396/428 |

FOREIGN PATENT DOCUMENTS

| | | |
|---|---|---|
| JP | 2007195296 A | 8/2007 |
| JP | 2009086513 A | 4/2009 |

(Continued)

OTHER PUBLICATIONS

International Search Report corresponding to PCT/JP2015/086473; dated Mar. 1, 2016; with partial English translation.
(Continued)

*Primary Examiner* — Stephone B Allen
*Assistant Examiner* — Rahman Abdur
(74) *Attorney, Agent, or Firm* — Cantor Colburn LLP

(57) ABSTRACT

Provided is an adaptor for attaching a portable terminal, said adaptor enabling a smartphone to be simply attached to and detached from a microscope. The present invention is provided with a first adaptor on the smartphone side, and a second adaptor on the microscope side. The first adaptor and the second adaptor, respectively have a first slide section and a second slide section, which are fitted to each other such that, in the straight line direction, the first slide section and the second slide section can mutually slide and can be attached to and detached from each other. As a result, the present invention makes it possible to easily attach and detach the smartphone to and from the microscope.

5 Claims, 12 Drawing Sheets

(51) Int. Cl.
*H04M 1/06* (2006.01)
*G03B 17/56* (2006.01)
*H04M 1/02* (2006.01)
*H04M 1/04* (2006.01)
*G02B 21/24* (2006.01)
*A61B 1/00* (2006.01)

(52) U.S. Cl.
CPC .............. *H04M 1/027* (2013.01); *H04M 1/04* (2013.01); *H04M 1/06* (2013.01); *H04M 1/21* (2013.01); *A61B 1/00131* (2013.01); *G02B 21/24* (2013.01); *G02B 21/248* (2013.01)

(58) Field of Classification Search
CPC ...... H04M 1/04; H04M 1/027; G03B 17/566; A61B 1/00131
USPC ........................................................ 359/363
See application file for complete search history.

(56) References Cited

FOREIGN PATENT DOCUMENTS

| | | |
|---|---|---|
| JP | 2012228011 A | 11/2012 |
| JP | 3183500 U | 4/2013 |
| JP | 2013160915 A | 8/2013 |
| JP | 2015200700 A | 11/2015 |
| KR | 101485509 B1 | 1/2015 |

OTHER PUBLICATIONS

JP Notice of Reasons for Rejection corresponding to Application No. 2016-538813; dated Nov. 7, 2017.
Extended European Search Report corresponding to Application No. 15904157.3-1020/3322164 PCT/JP2015086473; dated Feb. 20, 2019.

* cited by examiner

ADAPTOR FOR ATTACHING PORTABLE TERMINAL

CROSS REFERENCE TO RELATED APPLICATIONS

This is the U.S. national stage of application No. PCT/JP2015/086473, filed on Dec. 28, 2015. Priority under 35 U.S.C. § 119(a) and 35 U.S.C. § 365(b) is claimed from Japanese Application No. 2015-181428, filed Sep. 15, 2015, the disclosure of which is also incorporated herein by reference.

TECHNICAL FIELD

The present invention relates to an adaptor for attaching a camera-equipped mobile terminal to an optical instrument detachably.

BACKGROUND ART

This kind of adaptor for attaching a mobile terminal has conventionally been available (such as in PTL 1 and PTL 2). A conventional adaptor according to PTL 1, referred as a "connector", comprises a base portion on the side of a camera-equipped mobile phone and a magnification unit on the side of a microscope, wherein the magnification unit can be attached to the base portion by turning. According to the conventional connector of PTL 1, a camera-equipped mobile phone is attached to the base portion detachably, and then the magnification unit is attached to the base portion by turning and the magnification unit is attached to a barrel of a microscope detachably. The conventional connector according to PTL 1 is thus used by connecting a camera-equipped mobile phone and a microscope via the base portion and the magnification unit.

The conventional adaptor according to PTL 2, referred as a "joining adaptor", comprises a main body as well as a mobile terminal attaching part and an optical instrument attaching part that are provided back to back on the main body. According to the conventional adaptor in PTL 2, a mobile terminal equipped with a camera function can be attached to the main body via the mobile terminal attaching part, while an optical instrument can be attached to the main body via the optical instrument attaching part. The conventional adaptor according to PTL 2 is thus used by joining the mobile terminal equipped with the camera function and the optical instrument via the main body, the mobile terminal attaching part and the optical instrument attaching part.

CITATION LIST

Patent Literature

PTL 1

PTL 1: JP 2013-160915 A

PTL 2

PTL 2: JP 2015-200700 A

SUMMARY OF INVENTION

Technical Problem

It is important for such an adaptor for attaching a mobile terminal, such as the conventional connector in PTL 1 and the conventional joining adaptor in PTL 2, that a camera-equipped mobile terminal, such as the conventional camera-equipped mobile phone in PTL 1 and the conventional mobile terminal equipped with the camera function in PTL 2, can be easily attached and detached to/from an optical instrument, such as the conventional microscope in PTL 1 and the conventional optical instrument in PTL 2. A user needs to use a camera-equipped mobile terminal for phone conversation or the like when he receives an incoming call or the like while the camera-equipped mobile terminal is attached to an optical instrument and used for photographing or the like, for example. That is, there may arise a need that the camera-equipped mobile terminal is used for a primary function thereof such as the phone conversation even while the camera-equipped mobile terminal is attached to the optical instrument and used for a camera function or the like. In this case, it is important for the camera-equipped mobile terminal to be easily detached from the optical instrument. It is also important for the camera-equipped mobile terminal to be easily attached to the optical instrument.

A problem to be solved by the present invention is to provide an adaptor for attaching a portable terminal enabling the camera-equipped mobile terminal to be easily attached and detached to/from the optical instrument.

Solution to Problem

The present invention is characterized by comprising a first adaptor part for a camera-equipped mobile terminal and a second adaptor part for an optical instrument, the first adaptor part and the second adaptor part including a first slide portion and a second slide portion detachably and slidably engaged to each other in a straight line direction.

In the present invention, the first adaptor part and the second adaptor part may include a first stopper portion and a second stopper portion that come into contact with each other to allow the first adaptor part and the second adaptor part to be stopped at a predetermined position.

In the present invention, the first adaptor part and the second adaptor part may be immobilized at a predetermined position where the first stopper portion and the second stopper portion are in contact with each other by means of gravity on the first adaptor part.

In the present invention, the first adaptor part and the second adaptor part may include a first lock portion and a second lock portion by which the first adaptor part and the second adaptor part are locked at a predetermined stop position when the first stopper portion and the second stopper portion come into contact with each other.

In the present invention, the first adaptor part may be attached to a mobile terminal via a first attaching member provided separately from the mobile terminal or be provided integrally with the mobile terminal, and the second adaptor part may be attached to the optical instrument via a second attaching member provided separately from the optical instrument or be provided integrally with the optical instrument.

In the present invention, the first attaching member may be a case attached to the mobile terminal or a fixing tool fixed to the mobile terminal.

In the present invention, the second attaching member may be a member having an optical system and to be inserted into a barrel of the optical instrument, or a member fixed to an ocular lens or an object having a lens of the optical instrument.

Advantageous Effects of Invention

According to the present invention, it is provide an adaptor for attaching a camera-equipped mobile terminal enabling a camera-equipped mobile terminal to be easily attached and detached to/from the optical instrument.

DESCRIPTION OF EMBODIMENTS

Figure 8A:
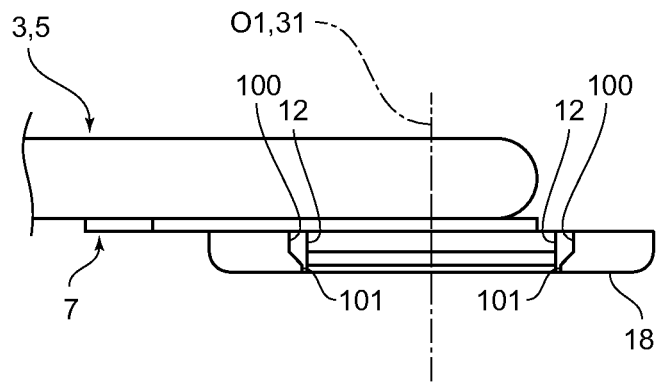
FIG. 8 is an explanatory diagram illustrating a state before the first adaptor part and the second adaptor part are attached and a state after the adaptor parts are attached completely.
Figure 8B:
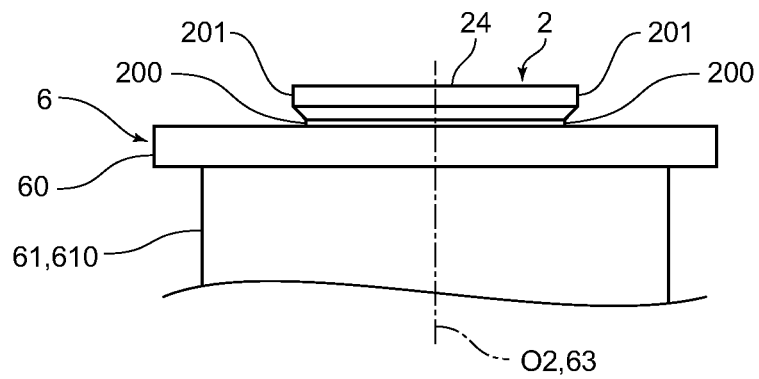
Figure 8C:
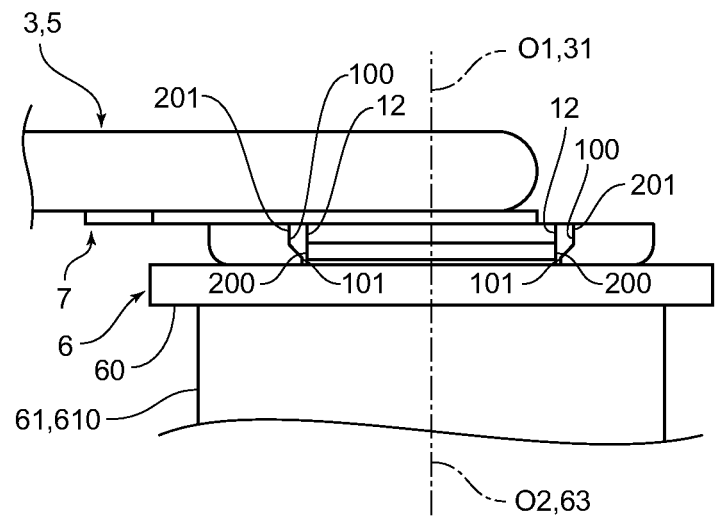
Figure 10:
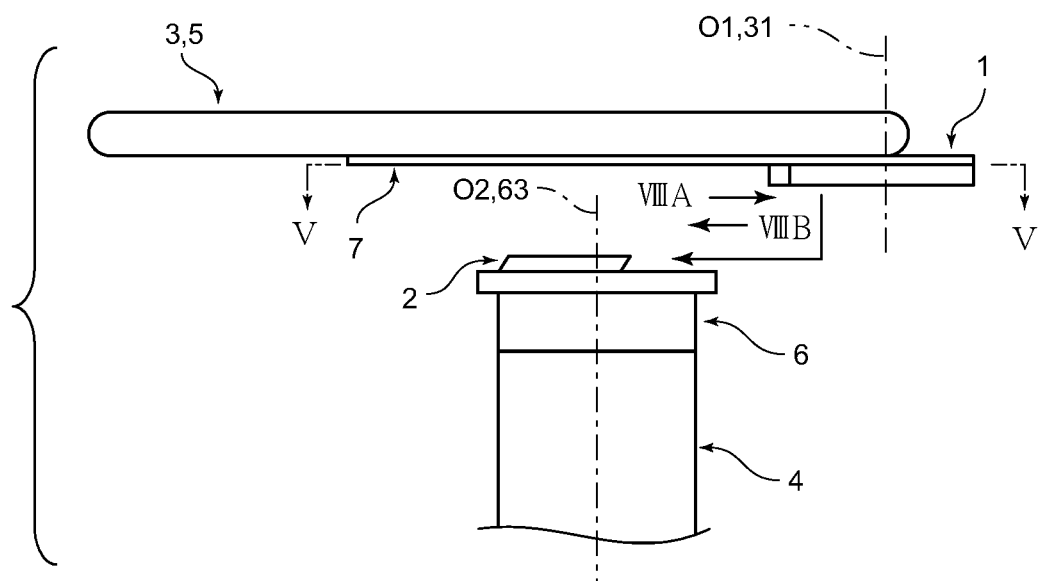
FIG. 10 is a side view illustrating the first adaptor part attached to the smartphone and the second adaptor part inserted into the barrel of the microscope (a side view corresponding to FIG. 9).
Figure 11:
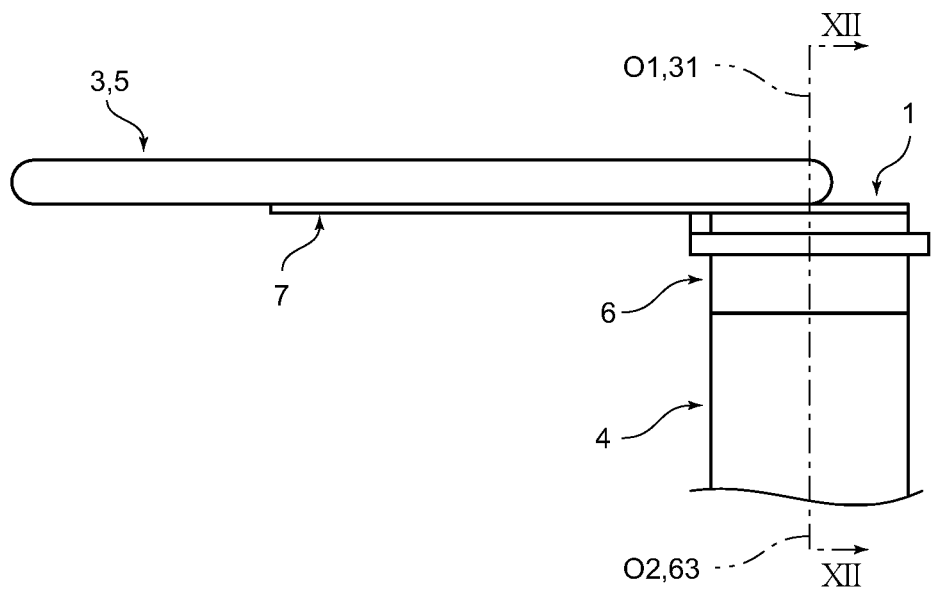
FIG. 11 is a side view illustrating a state in which the first adaptor part attached to the smartphone and the second adaptor part inserted into the barrel of the microscope are attached completely (a side view corresponding to FIG. 9).

Four embodiments of the adaptor for attaching a camera-equipped mobile terminal according to the present invention will be described below in detail with reference to the drawings. Hatching on a lens is omitted in the cross-sectional views in FIGS. 12 to 14 and 17. FIG. 8A is an explanatory diagram illustrating a first adaptor part (a view taken in the direction of arrow VIIIA in FIG. 10). FIG. 8B is an explanatory diagram illustrating a second adaptor part (a view taken in the direction of arrow VIIIB in FIG. 10). FIG. 8C is an explanatory diagram illustrating a state after the first adaptor part and the second adaptor part are attached completely.

Configuration of First Embodiment

FIGS. 1 to 16 illustrate a first embodiment of the adaptor for attaching a camera-equipped mobile terminal according to the present invention. A configuration of the adaptor according to the first embodiment will be described below. In the following explanation, There will be described an example where an optical instrument is a microscope.

Adaptor for Attaching a Camera-Equipped Mobile Terminal

The adaptor according to the first embodiment includes a first adaptor part 1 and a second adaptor part 2. The first adaptor part 1 includes first slide portions 10, a first stopper portion 11 and a first lock portion 12, and the second adaptor part 2 includes second slide portions 20, a second stopper portion 21 and a second lock portion 22.

The first adaptor part 1 is for a camera-equipped mobile terminal 3. The second adaptor part 2 is for an optical instrument 4. The adaptor according to the first embodiment is to attach the camera-equipped mobile terminal 3 to the optical instrument 4 detachably and easily by means of the first adaptor part 1 and the second adaptor part 2.

Smartphone 3

Here is exemplified a smartphone as the camera-equipped mobile terminal 3 (hereinafter referred to as a "smartphone 3"). The smartphone 3 is a mobile terminal equipped with a camera function, having a camera (not shown) built-in.

Figure 1:
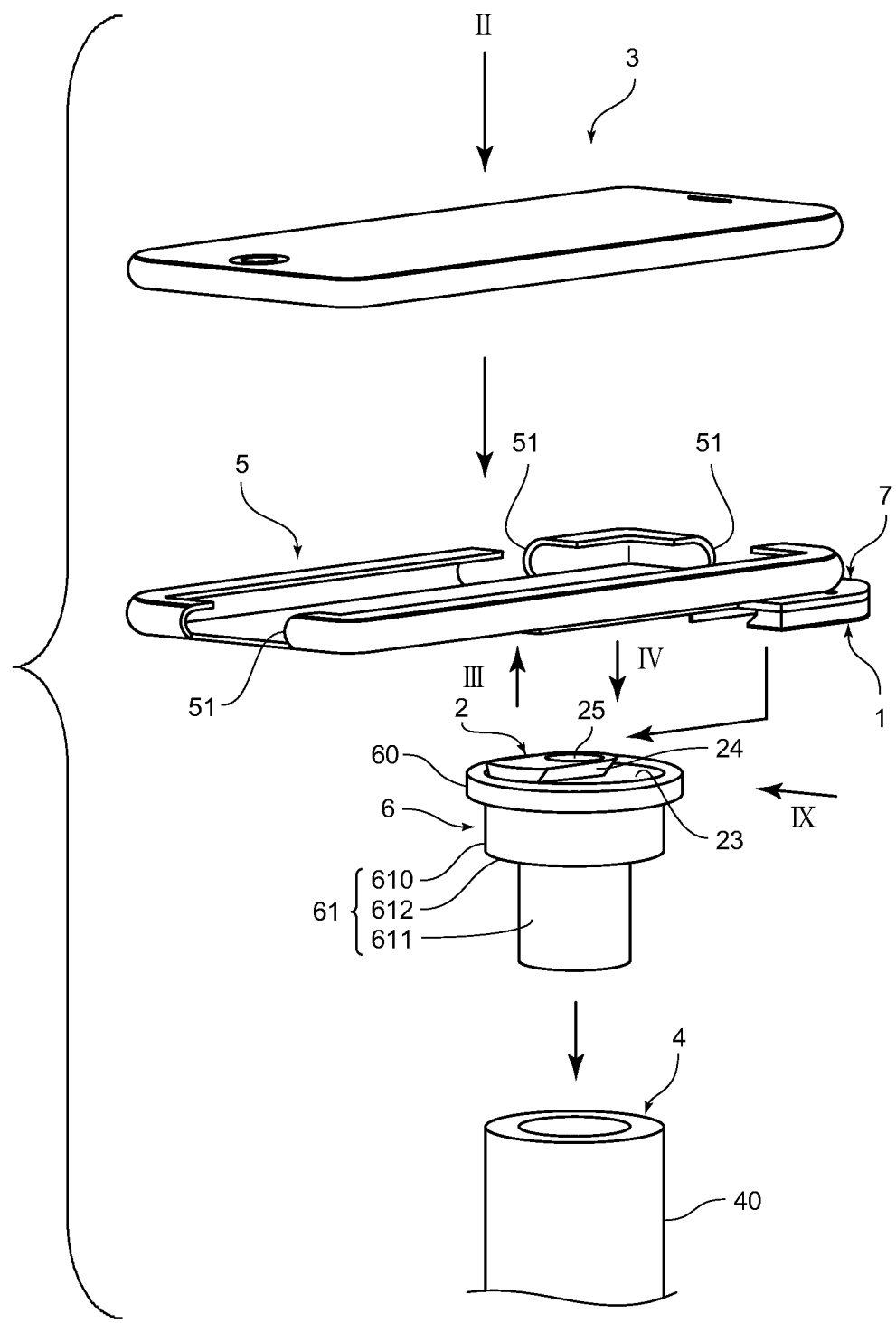
FIG. 1 is an exploded perspective view illustrating a first embodiment of the adaptor for attaching a camera-equipped mobile terminal according to the present invention.
Figure 2:
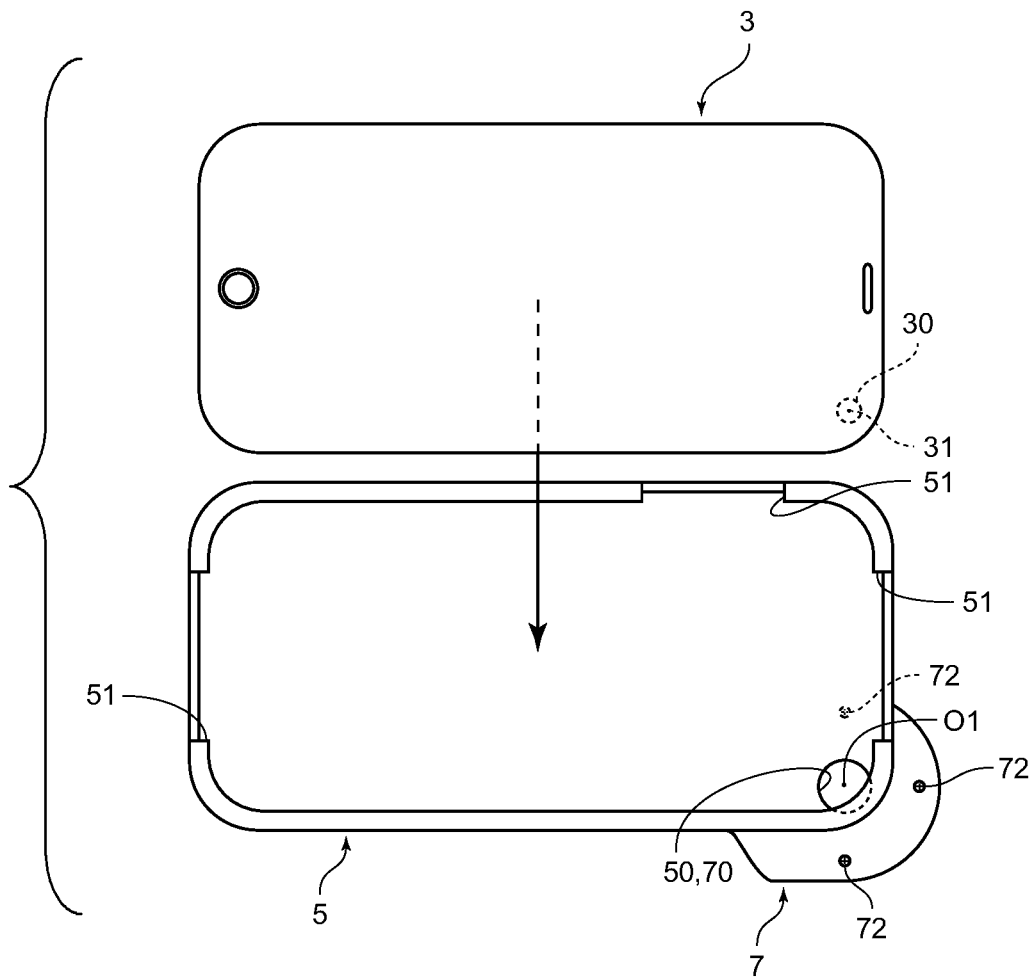
FIG. 2 is a plan view illustrating a first adaptor part and a case (hereinafter referred to as a "first adaptor part" collectively) and a smartphone (a view taken in the direction of arrow II in FIG. 1).
Figure 3:
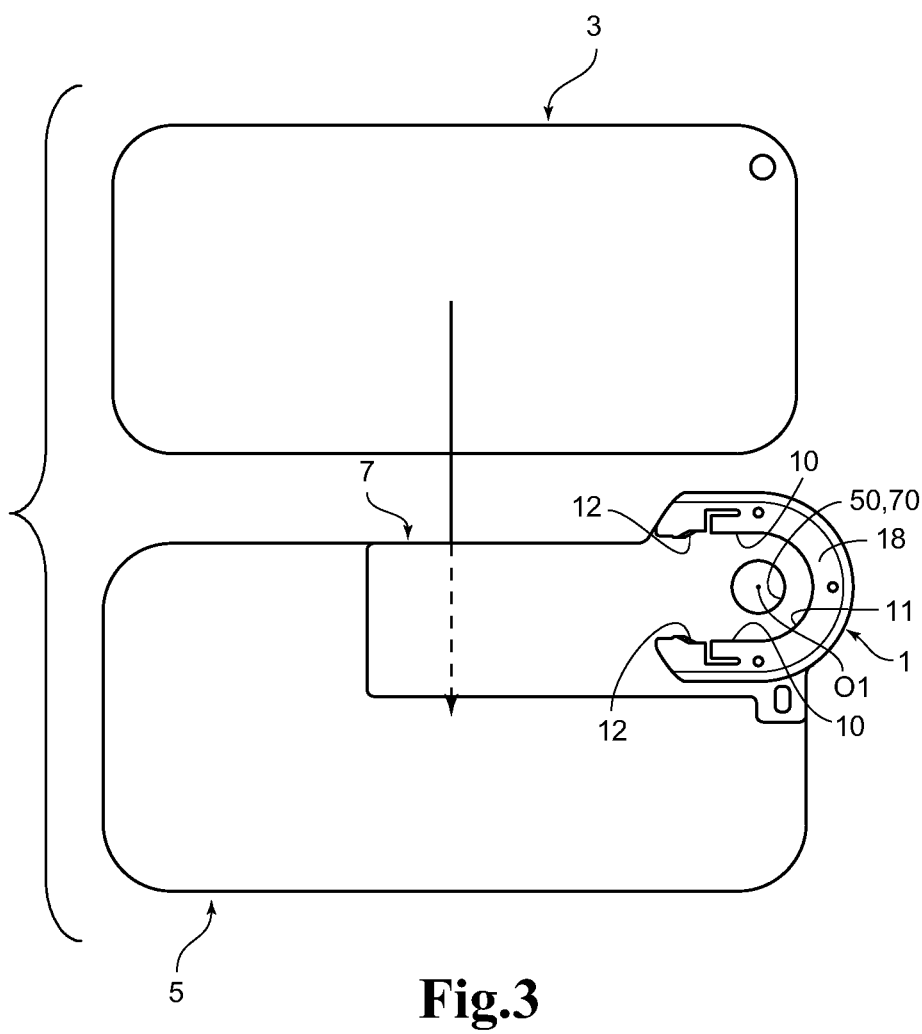
FIG. 3 is a bottom view illustrating the first adaptor part and the smartphone (a view taken in the direction of arrow III in FIG. 1).

As illustrated in FIGS. 1 to 3, a camera lens 30 is provided on one face (a bottom face in FIG. 1) of the smartphone 3. The camera lens 30 has an optical axis 31. The camera lens 30 is externally exposed at least at the time of imaging. A display is provided on another face (a top face in FIG. 1) of the smartphone 3. The smartphone 3 is provided with an operation button and a connecting part or the like to be connected with another device. The camera of the smartphone 3 is handled by operating the operation button or an operation image displayed in the display. The operation image displayed in the display may be operated by a touch operation in which a user directly touches the display or by a non-contact operation in which a user does not directly touch the display but hold his/her finger over the image.

Case 5

In the drawing, a reference sign "5" indicates a case attached to the smartphone 3. The case 5 is a case designed specifically for the smartphone 3. The case 5 protects the smartphone 3 against an impact or the like. The case 5 is shaped as a thin case as illustrated in FIGS. 1 to 3. A part on one face side of the case 5 (a part on a bottom face side in FIG. 1) is closed. A part on another face side of the case 5 (a part on a top face side in FIG. 1) is open. The case 5 is attached to the smartphone 3. This causes one face (a top face in FIG. 1) of the closed part of the case 5 and a face (the bottom face in FIG. 1) of the side of the camera lens 30 of the smartphone 3 to face each other. Moreover, a face (the top face in FIG. 1) of the side of the display of the smartphone 3 faces the open part of the case 5. Furthermore, a side wall of the case 5 surrounds a side face of the smartphone 3.

A through hole being a circular through hole 50 in this example is provided in a part of the closed part of the case 5 corresponding to the camera lens 30. As a result, image light (an optical image) to be captured by the camera reaches the camera lens 30 through the through hole 50. A center O1 of the through hole 50 is positioned on or near the optical axis 31 of the camera lens 30 of the smartphone 3. A notch 51 is provided on the side wall of the case 5 to allow for operating the operation button or connecting with another device.

Microscope 4

Figure 15:
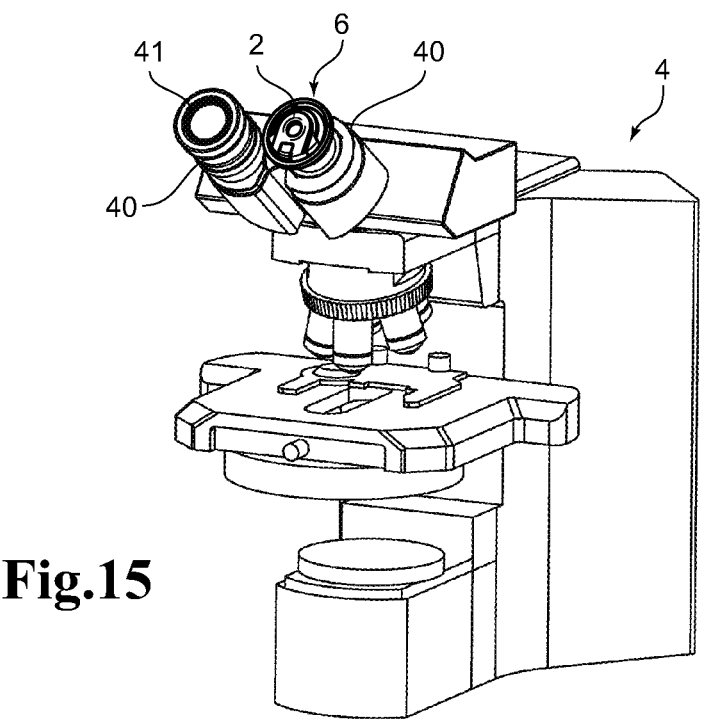
FIG. 15 is a perspective view illustrating a state in which the second adaptor part is inserted into the barrel of the microscope.
Figure 16:
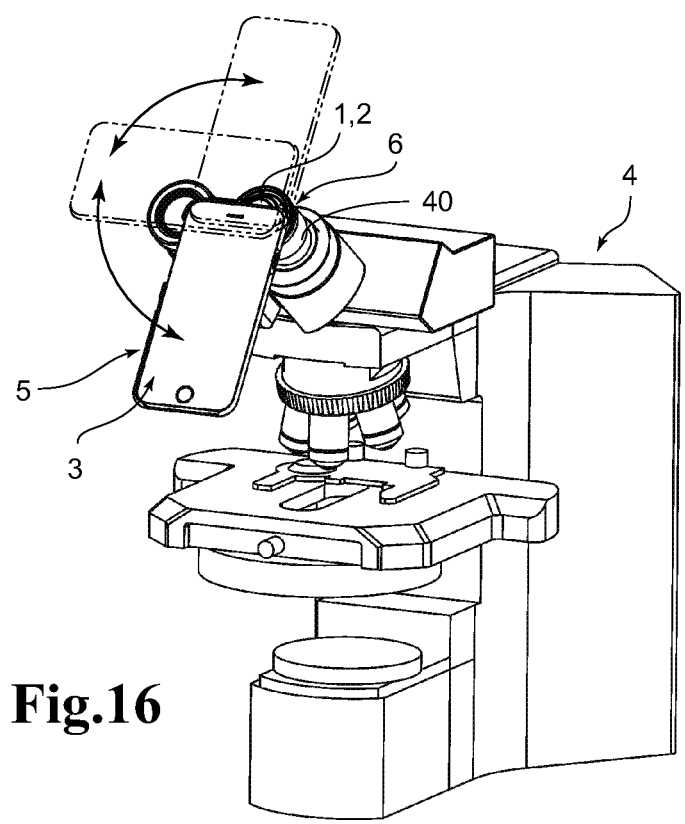
FIG. 16 is a perspective view illustrating a state in which the first adaptor part attached to the smartphone is attached to the second adaptor part inserted into the barrel of the microscope (an explanatory diagram illustrating a used state in the case where an optical instrument is the microscope).

Here is exemplified a microscope as the optical instrument 4 (hereinafter referred to as a "microscope 4"). The microscope 4 is a binocular microscope in this example as illustrated in FIGS. 15 and 16. The microscope 4 includes two barrels 40. An ocular lens unit (eyepiece) 41 is detachably inserted into each of the two barrels 40. In this example, the ocular lens unit 41 is removed from one of the barrels 40.

Optical Member 6

An optical member (an optical system adaptor) 6 is detachably inserted into the barrel 40 from which the ocular lens unit 41 is removed. The optical member 6 includes a ring 60, a cylinder portion 61 having a cylindrical shape, and a lens 62 of the optical system as illustrated in FIGS. 1 and 12 to 14.

Figure 12:
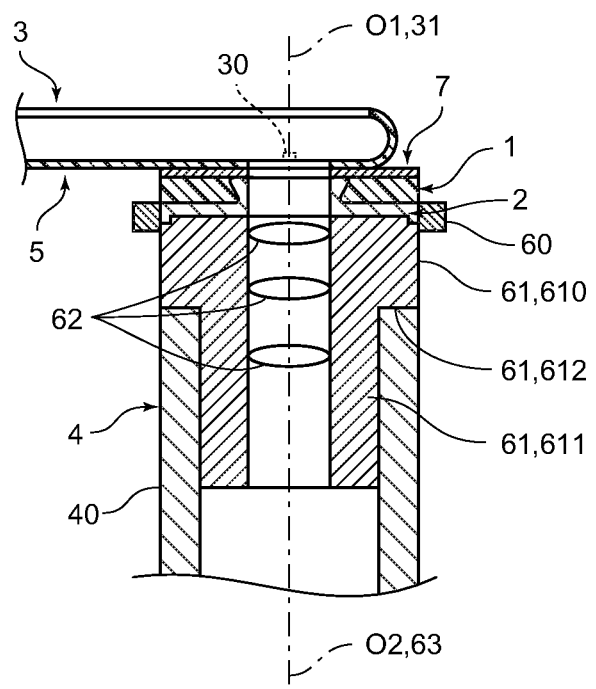
FIG. 12 is a cross-sectional view taken along line XII-XII of FIG. 11.
Figure 13:
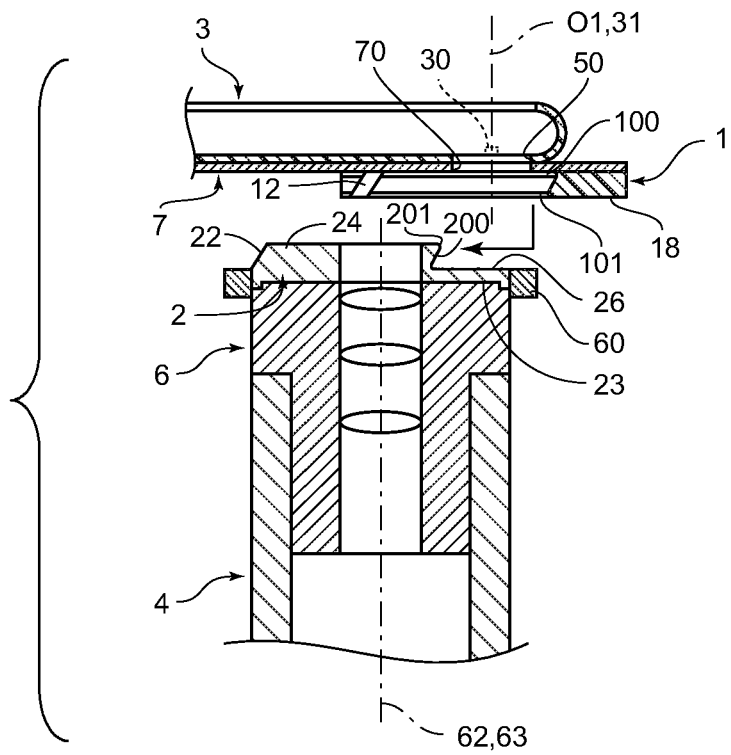
FIG. 13 is a cross-sectional view illustrating the first adaptor part attached to the smartphone and the second adaptor part inserted into the barrel of the microscope.
Figure 14:
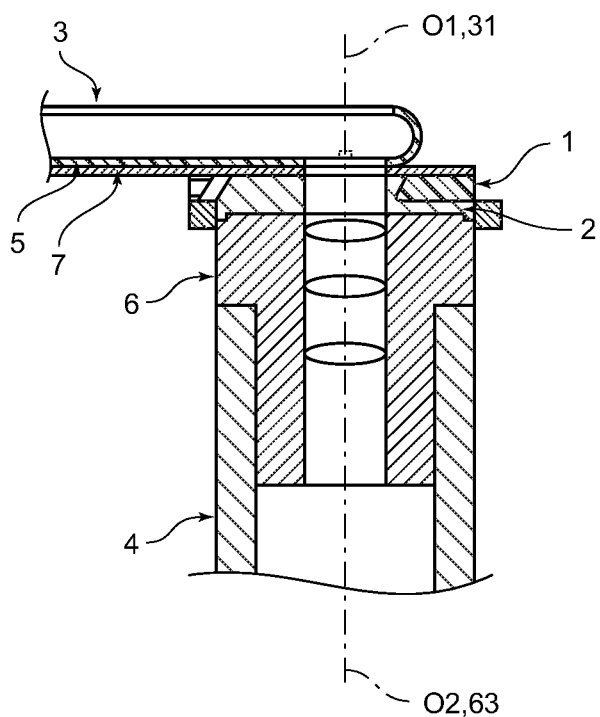
FIG. 14 is a cross-sectional view illustrating a state in which the first adaptor part attached to the smartphone and the second adaptor part inserted into the barrel of the microscope are attached completely (a cross-sectional view taken along line XIV-XIV of FIG. 7).

The cylinder portion 61 is formed of a larger diameter portion 610 at one end, a smaller diameter portion 611 at another end, and a stepped surface 612 between the larger diameter portion 610 and the smaller diameter portion 611. An outer diameter of the smaller diameter portion 611 is identical or substantially identical to an inner diameter of the barrel 40. An outer diameter of the larger diameter portion 610 is identical or substantially identical to an outer diameter of the barrel 40. Note that the outer diameter of the larger diameter portion 610 is not necessarily required to be identical to the outer diameter of the barrel 40. The smaller diameter portion 611 is inserted into the barrel 40. This allows the stepped surface 612 to be in contact with an end face of the barrel 40 as illustrated in FIGS. 12 to 14. At this time, friction between an outer peripheral face of the smaller diameter portion 611 and an inner peripheral face of the barrel 40 causes the optical member 6 to be fixed against the barrel 40 of the microscope 4 at an arbitrary position about a center line of the barrel 40.

The lens 62 is incorporated in the cylinder portion 61. The lens 62 is optically designed such that image light from an objective lens of the microscope 4 is optimal for the camera of the smartphone 3. The lens 62 has an optical axis 63.

First Adaptor Part 1

Figure 5:
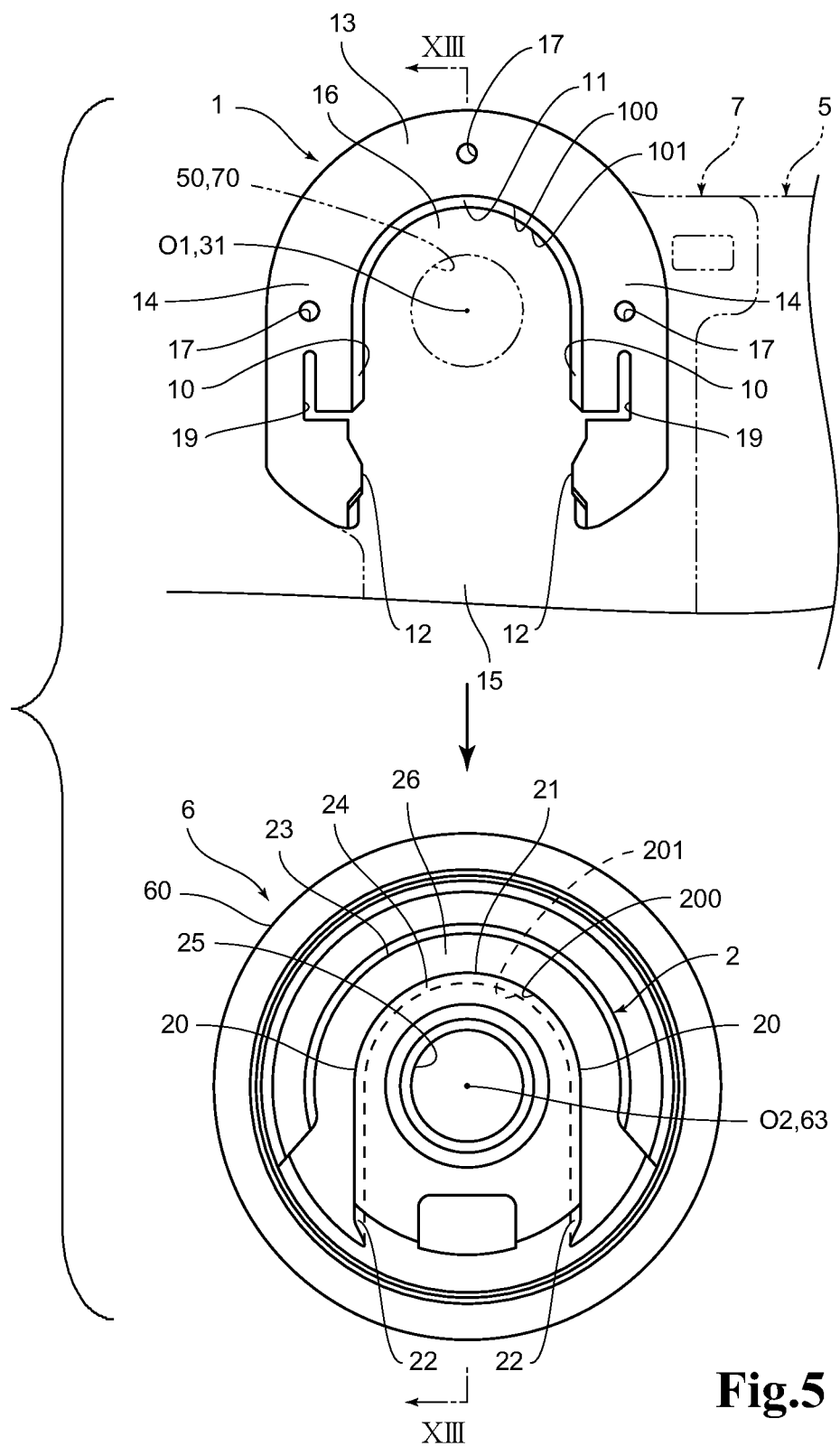
FIG. 5 is an explanatory diagram illustrating the first adaptor part and the second adaptor part (a view taken in the direction of arrows V-V line in FIG. 10).

As illustrated in FIGS. 3, 5 to 7, 8A and 8C, and 12 to 14, the first adaptor part 1 is made of a sheet member having elasticity, for example, a synthetic resin such as POM. The first adaptor part 1 is U-shaped as illustrated in FIGS. 3 and 5 when viewed in the direction of arrow III in FIG. 1 and arrows V-V line in FIG. 10. That is, one end portion of the first adaptor part 1 forms a closed part 13 in the shape of an arc (a semi-circular arc in this example). Two middle pieces of the first adaptor part 1 form two straight arm portions 14 that are parallel or substantially parallel to each other. Another end of the first adaptor part 1 forms an opening 15. A tongue-shaped recess 16 is formed in a central part of the first adaptor part 1. A screw hole 17 in the shape of a small circle is provided at each of three sites on the closed part 13, three sites including the middle and two ends of the closed part. One face (the bottom face in FIG. 1 and the face as viewed in the direction of arrow III in FIG. 1) of the first adaptor part 1 forms a planar first slide surface 18. A corner of the one face of the first adaptor part 1 forms approximately a quarter of a circle. On the other hand, another face (the top face in FIG. 1 and the face as viewed in the direction of arrows V-V line in FIG. 10) of the first adaptor part 1 forms a plane throughout the entire surface.

The first slide portions 10 are provided on respective side faces of the recess 16, that is, inner faces of the two straight arm portions 14 of the first adaptor part 1. The first stopper portion 11 is provided on a side face of the recess 16, that is, an inner face of the arc-shaped closed part 13 of the first adaptor part 1. The first slide portions 10 and the first stopper portion 11 form a rail-like structure including a groove (guide groove) 100 and a projection (guide projection) 101. The groove 100 is provided on the other face side of the first adaptor part 1. The projection 101 is provided on the one face side of the first adaptor part 1.

The first lock portion 12 is provided on a side face of the recess 16, the side face being an inner face of each of the two arm portions 14 of the first adaptor part 1 on the side of the opening 15. The first lock portion 12 forms a projecting shape projecting inward from the side face of the recess 16. As illustrated in FIGS. 13 and 14, the first lock portion 12 is inclined from the side of the opening 15 to the side of the closed part 13 from the one face to the other face of the first adaptor part 1. As illustrated in FIGS. 8A and 8C, tips of the two first lock portions 12 facing each other project inward relative to the bottom of the groove 100 and project slightly inward relative to the top of the projection 101.

A slit 19 is provided at a site from the first lock portion 12 to the side of the closed part 13 in each of the two arm portions 14. The slit 19 is provided to some extent along a shorter direction of the arm portion 14 from the recess 16 as well as provided along a longer direction of the arm portion 14 to the side of the closed part 13. The slit 19 is provided such that the first lock portion 12 of the arm portion 14 undergoes an elastic deformation in the direction of a solid arrow indicated in FIGS. 6 and 7 with respect to the side of the closed part 13. Note that the shape of the slit 19 is not to be specifically restricted. Moreover, the slit 19 is not to be necessarily provided as long as the elastic deformation of the first lock portion 12 can be achieved without the slit 19.

Fixing Plate 7

A reference sign "7" in the drawing indicates a fixing plate that fixes the first adaptor part 1 to the case 5. The fixing plate 7 is made of a rigid sheet member as illustrated in FIGS. 1 to 3 and 5 to 14. The fixing plate 7 is an aluminum plate in this example. One face (a top face in FIGS. 1 and 8 to 14) of the fixing plate 7 is fixed by an adhesive or the like on another face (a bottom face in FIGS. 1 and 8 to 14) of the closed part of the case 5, the other face being a corner of the case 5 at which the through hole 50 is provided.

The fixing plate 7 is provided with three small circular insertion holes 71 corresponding to the three screw holes 17, respectively. Three screws 72 (illustrated only in FIG. 2) are inserted into the three insertion holes 71. The three screws 72 are screwed into the three screw holes 17. The other face of the first adaptor part 1 is thus fixed to another face (a bottom face in FIGS. 1 and 8 to 14) of the fixing plate 7. As a result, the first adaptor part 1 is fixed to the case 5 via the fixing plate 7. Moreover, the first adaptor part 1 is attached to the smartphone 3 via the fixing plate 7 and the case 5 being a first attaching member provided separately from the smartphone 3.

A circular through hole 70 is provided in the fixing plate 7. The diameter of the through hole 70 is equal or substantially equal to the diameter of the through hole 50 in the case 5 and smaller than the diameter of the closed part 13 of the first adaptor part 1. The center of the through hole 70 in the fixing plate 7, the center O1 of the through hole 50 in the case 5, and the center of the closed part 13 of the first adaptor part 1 correspond or substantially correspond with one another on or near the optical axis 31 of the camera lens 30 of the smartphone 3. Note that the through hole 70 may be formed in the shape of not only the circle but an ellipse or another shape. Moreover, the three insertion holes 71 are arranged at equal intervals or substantially equal intervals (with the central angle of approximately 90°) on a circle of an appropriate diameter with the center corresponding with the center of the through hole 70.

Second Adaptor Part 2

The second adaptor part 2 comprises a disk-shaped plate portion 23 and a tongue-shaped protrusion 24 as illustrated in FIGS. 1 and 4 to 14. The protrusion 24 is provided integrally with one face (a top face in FIGS. 1 and 12 to 14) of the plate portion 23. A through hole being a circular through hole 25 in this example is provided at the center of the second adaptor part 2. The one face of the plate portion 23 forms a second slide surface 26. The second slide surface 26 and the first slide surface 18 are configured to slide with respect to each other.

The plate portion 23 is attached to one end of the cylinder portion 61. The second adaptor part 2 is fixed to the optical member 6 as a result. Accordingly, image light from the lens 62 optimal for the camera of the smartphone 3, that is the image light from the objective lens of the microscope 4, passes through the through hole 25. A center O2 of the through hole 25 is positioned on or near the optical axis 63 of the lens 62 of the optical member 6. Moreover, the second adaptor part 2 is attached to the microscope 4 via the optical member 6 as a second attaching member provided separately from the microscope 4.

The protrusion 24 has substantially the same shape as the recess 16 of the first adaptor part 1. That is, an outer face at one end portion of an arc (a semi-circular arc in this example) of the protrusion 24 substantially corresponds with an inner face of the closed part 13 of the first adaptor part 1. Both outer faces of a straight middle part of the protrusion 24 substantially correspond with inner faces of the two arm portions 14 of the first adaptor part 1. An outer face of another end of the protrusion 24 forms an arc shape.

The second slide portions 20 are provided on the outer faces of the straight middle part of the protrusion 24 of the second adaptor part 2 respectively. The second stopper portion 21 is provided on the outer face at one end portion of the arc shape of the protrusion 24 of the second adaptor part 2. The second slide portions 20 and the second stopper portion 21 form a rail-like structure including a groove (guide groove) 200 and a projection (guide projection) 201. The groove 200 is provided on the side of the plate portion 23. The projection 201 is provided on a side opposite to the side of the plate portion 23.

The second lock portion 22 is provided at each of two sites corresponding to the tips of the two second slide portions 20, the two sites corresponding to the outer face at another end of the arc shape of the protrusion 24 of the second adaptor part 2. As illustrated in FIGS. 13 and 14, the outer face at the other end of the protrusion 24 including the second lock portion 22 is inclined from the other end portion side of the protrusion 24 to the one end side of the protrusion 24 from the side of the plate portion 23 to the side opposite to the side of the plate portion 23. The inclination of the second lock portion 22 and the first lock portion 12 correspond or substantially correspond with each other.

First Adaptor Part 1 and Second Adaptor Part 2

The groove 100 of the first slide portions 10 of the first adaptor part 1 and the projection 201 of the second slide portions 20 of the second adaptor part are fitted together. The projection 101 of the first slide portions 10 of the first adaptor part 1 and the groove 200 of the second slide portions 20 of the second adaptor part are fitted together. Therefore, the first adaptor part 1 and the second adaptor part are detachably and slidably fitted to each other in a straight line direction.

The faces of the groove 100 and the projection 101 of the first stopper portion 11 of the first adaptor part 1 and the faces of the projection 201 and the groove 200 of the second stopper portion 21 of the second adaptor part are to be in contact with each other. As a result, the first adaptor part 1 and the second adaptor part are stopped at a predetermined position (a proper position).

The first lock portion 12 of the first adaptor part 1 and the second lock portion 22 of the second adaptor part 2 are in a locked state when the first stopper portion 11 of the first adaptor part 1 and the second stopper portion 21 of the second adaptor part are in contact with each other. As a result, the first adaptor part 1 and the second adaptor part are locked at a predetermined position.

Workings of First Embodiment

The adaptor according to the first embodiment is configured as described above. The workings of the adaptor will be described below.

Figure 4:
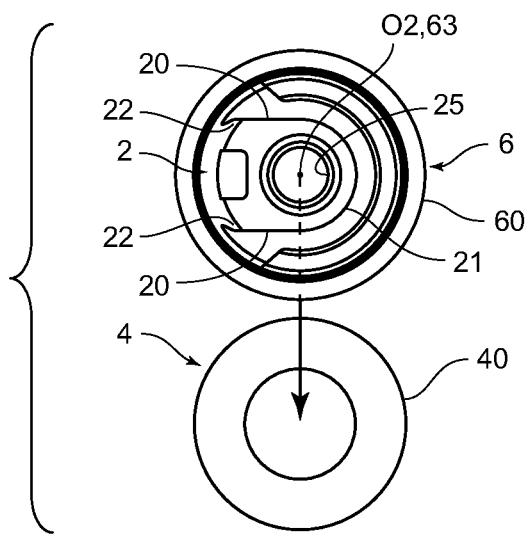
FIG. 4 is a plan view illustrating a second adaptor part and a member including an optical system (hereinafter referred to as a "second adaptor part" collectively) and a barrel of a microscope (a view taken in the direction of arrow IV in FIG. 1).
Figure 9:
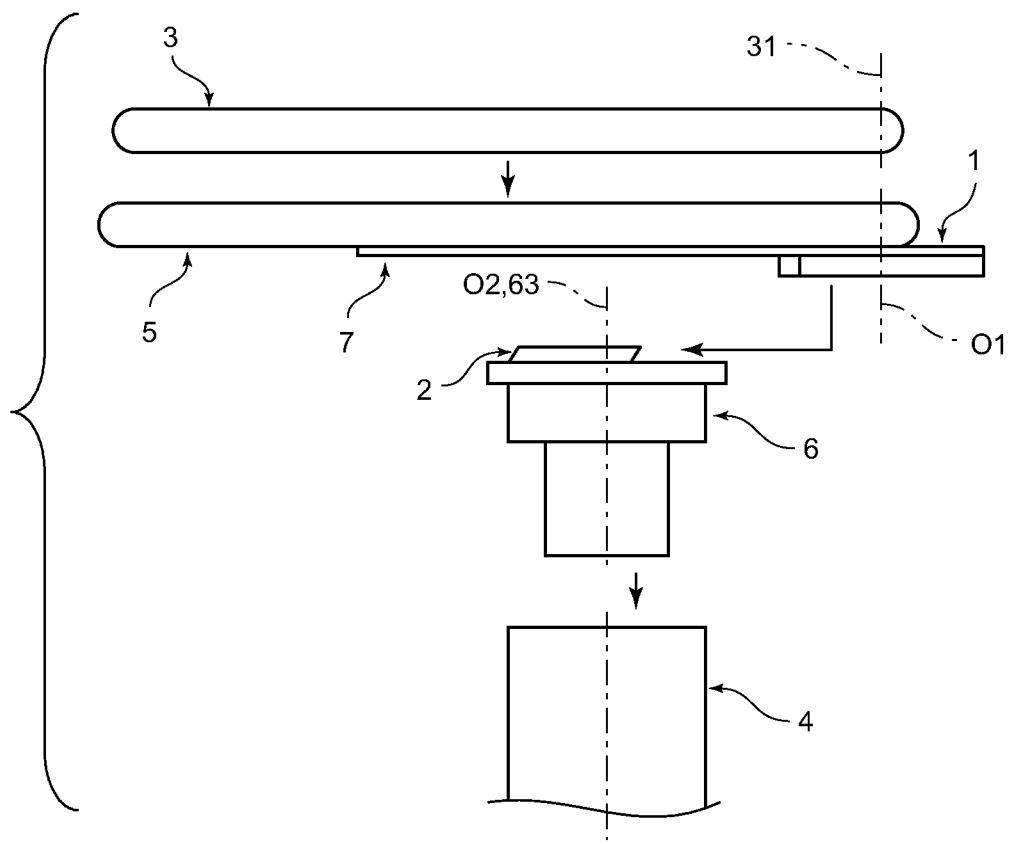
FIG. 9 is a side view illustrating the first adaptor part, the smartphone, the second adaptor part, and the barrel of the microscope (a view taken in the direction of arrow IX in FIG. 1).

As illustrated in FIGS. 1 to 3 and 9, the case 5 with the first adaptor part 1 fixed thereto via the fixing plate 7 is detachably attached to the smartphone 3. As illustrated in FIGS. 1, 4 and 9, the optical member 6 with the second adaptor part 2 fixed thereto is detachably inserted into the barrel 40 of the microscope 4 from which the ocular lens unit 41 is removed. As illustrated in FIGS. 1, 5, 9, 10, and 13, the first adaptor part 1 on the side of the smartphone 3 is attached to the second adaptor part 2 on the side of the microscope 4 detachably along the straight line direction.

First, as indicated by a solid arrow in FIGS. 1, 5, 9, 10 and 13, the first slide surface 18 of the first adaptor part 1 is placed on the second slide surface 26 of the second adaptor part 2. At the same time, the first adaptor part 1 on the side of the opening 15 is slid in the straight line direction toward the side of the one end portion of the semi-circular arc of the protrusion 24 of the second adaptor part 2. The groove 100 and the projection 101 of the first slide portions 10 of the first adaptor part 1 and the projection 201 and the groove 200 of the second slide portions 20 of the second adaptor part 2 are then mutually fitted slidably in the straight line direction.

Figure 6:
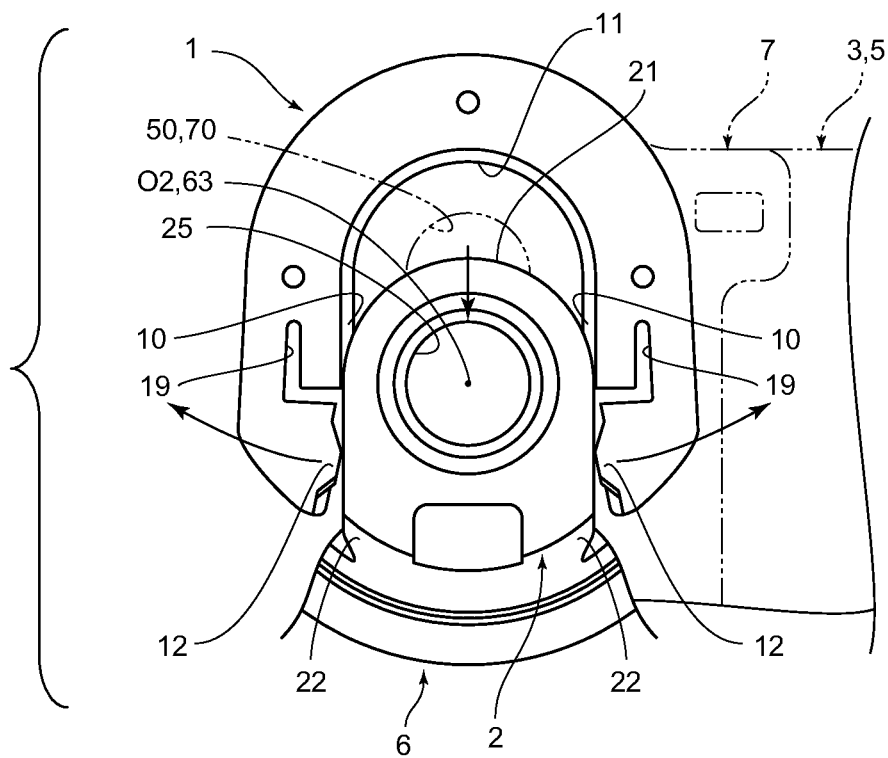
FIG. 6 is an explanatory diagram illustrating a state in which the first adaptor part and the second adaptor part are in the process of being attached (an explanatory diagram corresponding to FIG. 5).

Next, the first adaptor part 1 is slid with respect to the second adaptor part 2. As illustrated in FIG. 6, the first lock portions 12 of the first adaptor part 1 comes into contact with the second slide portions 20 of the second adaptor part 2. The first lock portion 12 of the two arm portions 14 of the first adaptor part 1 then opens outward to the side of the closed part 13 in the direction of a solid arrow in FIG. 6 and undergoes elastic deformation. That is, a part from the slit 19 to the side of the first lock portion 12 of the arm portion 14 opens outward to a part from the slit 19 to the side of the closed part 13 of the arm portion 14.

Figure 7:
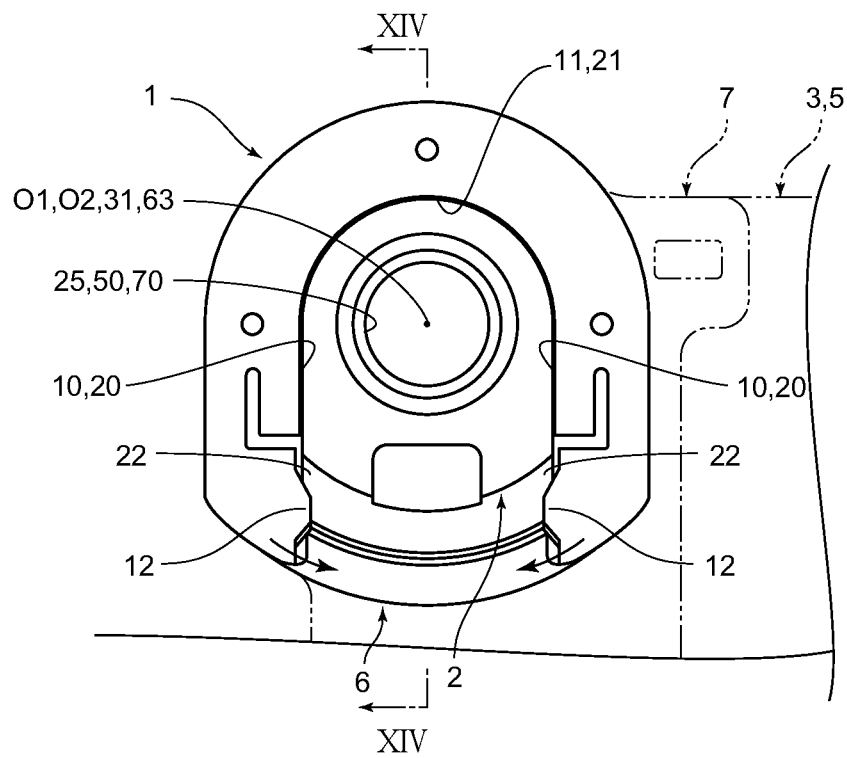
FIG. 7 is an explanatory diagram illustrating a state in which the first adaptor part and the second adaptor part are attached completely (an explanatory diagram corresponding to FIG. 5).

The first adaptor part 1 is further slid with respect to the second adaptor part 2. As illustrated in FIG. 7, the groove 100 and the projection 101 of the first stopper portion 11 of the first adaptor part 1 and the projection 201 and the groove 200 of the second stopper portion 21 of the second adaptor part 2 come into contact with each other. The first adaptor part 1 and the second adaptor part 2 are then stopped at the predetermined position. As a result, as illustrated in FIG. 14, the optical axis 31 of the camera lens 30 of the smartphone 3 on the side of the first adaptor part 1 corresponds or substantially corresponds with the optical axis 63 of the optical member 6 on the side of the second adaptor part 2.

At this time, when the first stopper portion 11 and the second stopper portion 21 come into contact with each other as illustrated in FIG. 7, the first lock portion 12 opening outward and undergoing elastic deformation closes inward in the direction of a solid arrow in FIG. 7 and is elastically restored to an original state (a state illustrated in FIG. 5). Then, as illustrated in FIGS. 7 and 14, the two inclined first lock portions 12 of the first adaptor part come into contact with the two inclined second lock portions 22 of the second adaptor part 2. The first adaptor part 1 and the second adaptor part 2 are thus mutually locked at a predetermined stop position. The correspondence between the optical axis 31 of the camera lens 30 of the smartphone 3 and the optical axis 63 of the optical member 6 is also locked. Accordingly, the smartphone 3 can be easily attached to the microscope 4 via the first adaptor part 1 and the second adaptor part 2.

The correspondence between the optical axis 31 of the camera lens 30 of the smartphone 3 and the optical axis 63 of the optical member 6 then causes the image light from the objective lens of the microscope 4 to transmit through the lens 62 of the optical member 6 and be the image light optimal for the camera of the smartphone 3. The image light optimal for the camera passes through the through hole 25 of the second adaptor part 2, the through hole 50 of the case 5, the through hole 70 of the fixing plate 7 and the recess 16 of the first adaptor part 1 to reach the camera lens 30 of the smartphone 3.

Here, there may arise a need that the smartphone 3 is used for a primary function thereof such as a phone conversation even while the phone is attached to the microscope 4 and used for a camera function or the like. That is, the smartphone 3 needs to be detached from the microscope 4 when there is an incoming call or the like while the smartphone 3 is attached to the microscope 4 and used for photographing or the like.

At this time, the first adaptor part 1 on the side of the smartphone 3 is slid with respect to the second adaptor part 2 on the side of the microscope 4 in the straight line direction oppositely to the direction of the solid arrow illustrated in FIGS. 1, 5, 9, 10, and 13. The two first lock portions 12 open outward (toward the side opposite to the direction of the solid arrow in FIG. 7) when the force of sliding the first adaptor part 1 is larger than the elastic force of the two first lock portions 12 elastically being in contact with the two second lock portions 22. Accordingly, the first slide portions 10 and the second slide portions 20 slide mutually. The smartphone 3 is detached from the microscope 4 at a point when the first slide portions 10 and the second slide portions 20 are released from the mutually fitted state. The smartphone 3 can be easily detached from the microscope 4 as a result.

Effects of First Embodiment

The adaptor according to the first embodiment is configured and works as described above. The effect of the adaptor will be described below.

The adaptor according to the first embodiment includes the first adaptor part 1 on the side of the smartphone 3 and the second adaptor part 2 on the side of the microscope 4, where the first adaptor part 1 and the second adaptor part 2 have the first slides portion 10 and the second slides portion 20 that are detachably and slidably fitted mutually in the straight line direction. The adaptor according to the first embodiment can thus cause the first adaptor part 1 and the second adaptor part 2 to slide with respect to each other by causing the first slide portions 10 of the first adaptor part 1 on the side of the smartphone 3 and the second slide portions 20 of the second adaptor part 2 on the side of the microscope 4 to be slidably fitted mutually. As a result, the adaptor according to the first embodiment can easily attach the smartphone 3 to the microscope 4 by sliding the first adaptor part 1 and the second adaptor part 2 with respect to each other. Moreover, the adaptor according to the first embodiment can easily detach the smartphone 3 from the microscope 4 by sliding the first slide portions 10 and the second slide portions 20 mutually to release the fitted state.

The first adaptor part 1 and the second adaptor part 2 of the adaptor according to the first embodiment have the first stopper portion 11 and the second stopper portion 21 that come into contact with each other to stop the first adaptor part 1 and the second adaptor part 2 at a predetermined position. The adaptor according to the first embodiment can thus stop the first adaptor part 1 and the second adaptor part 2 at the predetermined position by bringing the first stopper portion 11 and the second stopper portion 21 into contact with each other. As a result, the mobile terminal attaching adaptor according to the first embodiment can cause the optical axis 31 of the camera lens 30 of the smartphone 3 on the side of the first adaptor part 1 to correspond or substantially correspond with the optical axis 63 of the optical member 6 on the side of the second adaptor part 2.

The first adaptor part 1 and the second adaptor part 2 of the mobile terminal attaching adaptor according to the first embodiment have the first lock portion 12 and the second lock portion 22 by which the first adaptor part 1 and the second adaptor part 2 are locked at a predetermined stop position when the first stopper portion 11 and the second stopper portion 21 come into contact with each other. Therefore, the mobile terminal attaching adaptor according to the first embodiment can surely position the first adaptor part 1 and the second adaptor part 2 at the predetermined stop position by the first lock portion 12 and the second lock portion 22. As a result, the mobile terminal attaching adaptor according to the first embodiment can surely maintain the correspondence between the optical axis 31 of the camera lens 30 of the smartphone 3 and the optical axis 63 of the optical member 6 on the side of the second adaptor part 2.

Moreover, the first adaptor part 1 of the adaptor according to the first embodiment is attached to the smartphone 3 via the fixing plate 7 and the case 5 being the first attaching member provided separately from the smartphone 3. The adaptor according to the first embodiment can thus attach the first adaptor part 1 to the smartphone 3 easily, surely, and accurately.

The second adaptor part 2 of the adaptor according to the first embodiment is attached to the microscope 4 via the optical member 6 being the second attaching member provided separately from the microscope 4. The adaptor according to the first embodiment can thus attach the second adaptor part 2 to the microscope 4 easily, surely, and accurately.

Second Embodiment

Figure 17:
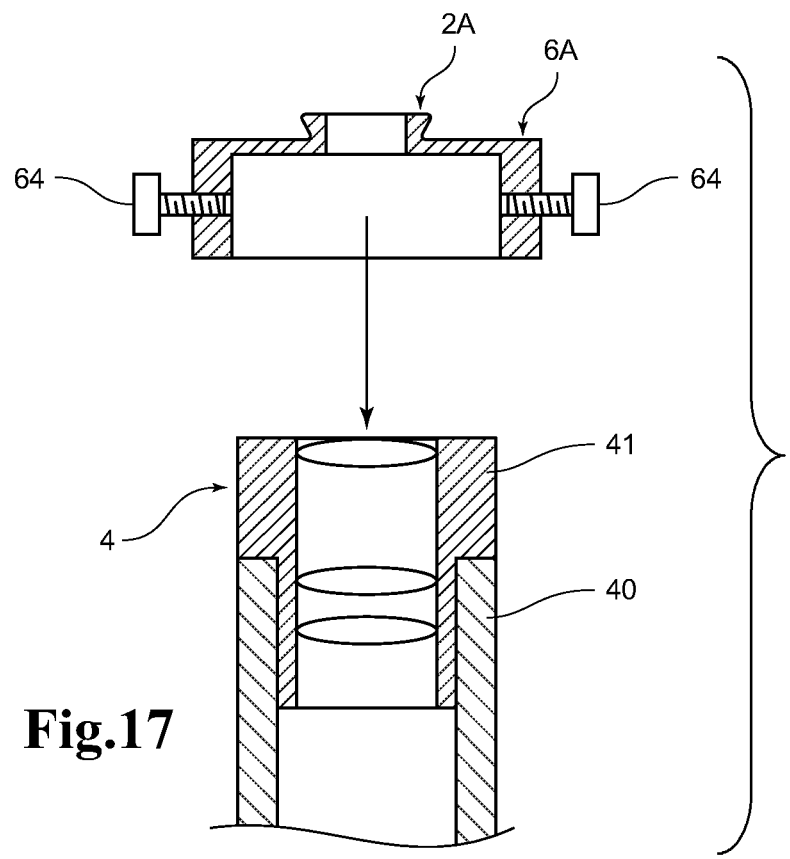
FIG. 17 is a cross-sectional view illustrating a second embodiment of the adaptor for attaching a camera-equipped mobile terminal according to the present invention (a cross-sectional view illustrating a variation of the second adaptor part).

FIG. 17 is a cross-sectional view illustrating a second embodiment of the adaptor for attaching portable terminal according to the present invention. The adaptor according to the second embodiment comprises a modified second adaptor part 2A. In FIG. 17, components indicated by same reference signs as in FIGS. 1 to 16 indicate the same components as ones therein.

The second adaptor part 2 of the adaptor according to the first embodiment is fixed to the optical member 6 having the lens 62 (optical system) and attached to the barrel 40 of the microscope 4 via the optical member 6. On the other hand, the second adaptor part 2A of the adaptor according to the second embodiment is fixed to a member 6A not having an optical system and attached to an ocular lens unit 41 of a microscope 4 via the member 6A. A reference sign "64" in FIG. 17 indicates a screw used to attach the member 6A in one with the second adaptor part 2A to the ocular lens unit 41.

The adaptor according to the second embodiment can achieve the effect substantially similar to the effect of the adaptor according to the first embodiment. That is, the second adaptor part 2A of the adaptor according to the second embodiment can be detachably and slidably fitted to a first adaptor part 1 mutually in a straight line direction as with the second adaptor part 2 of the adaptor according to the first embodiment.

Third Embodiment

Figure 18:
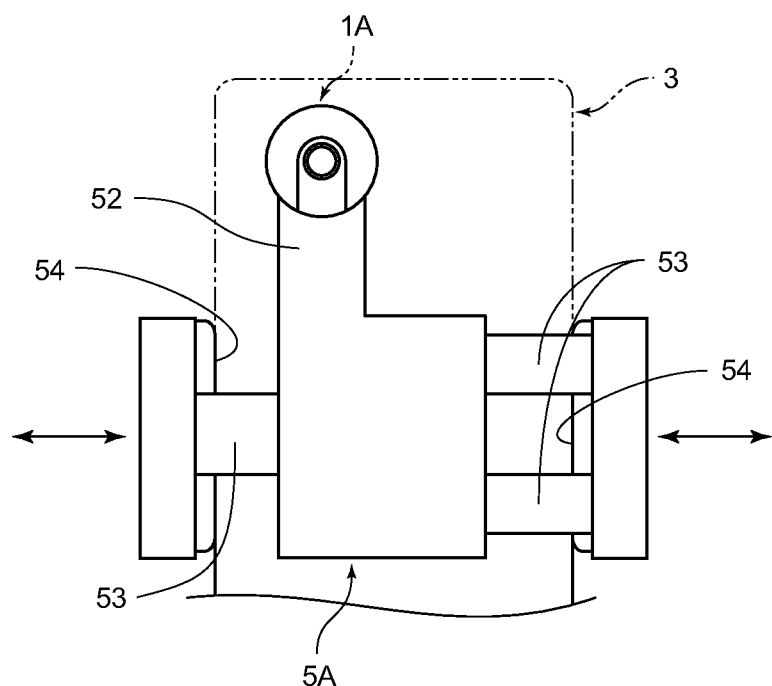
FIG. 18 is an explanatory diagram illustrating a third embodiment of the adaptor for attaching a camera-equipped mobile terminal according to the present invention (an explanatory diagram illustrating a variation of the first adaptor part).

FIG. 18 is an explanatory diagram illustrating a third embodiment of the adaptor for attaching portable terminal according to the present invention. The adaptor according to the third embodiment comprises a modified first adaptor part 1A. In FIG. 18, components indicated by same reference signs as in FIGS. 1 to 17 indicate the same components as ones therein.

The first adaptor part 1 of the adaptor according to the first embodiment is fixed to the case 5 via the fixing plate 7 and attached to the smartphone 3 via the case 5. On the other hand, the first adaptor part 1A of the adaptor according to the third embodiment is attached to a smartphone 3 via a fixing tool 5A. The fixing tool 5A includes a body 52, two slide arms 53, and a holding part 54. The first adaptor part 1A is fixed to the body 52. The two slide arms 53 are attached to the body 52 to be able to slide in a straight line direction (a direction of a solid arrow in FIG. 18). The holding part 54 is fixed to each of the two slide arms 53. The two slide arms 53 are slid to allow the two holding parts 54 to hold both sides of the smartphone 3. The fixing tool 5A is thus fixed to the smartphones 3 of various sizes. As a result, the first adaptor part 1A is attached to the smartphone 3 via the fixing tool 5A.

The adaptor according to the third embodiment can achieve the effect substantially similar to the effect of the adaptors according to the first and second embodiments. That is, the first adaptor part 1A of the adaptor according to the third embodiment can be detachably and slidably fitted to second adaptors part 2 and 2A mutually in the straight line direction as with the first adaptor part 1 of the adaptors according to the first and second embodiments.

Fourth Embodiment

Figure 19:
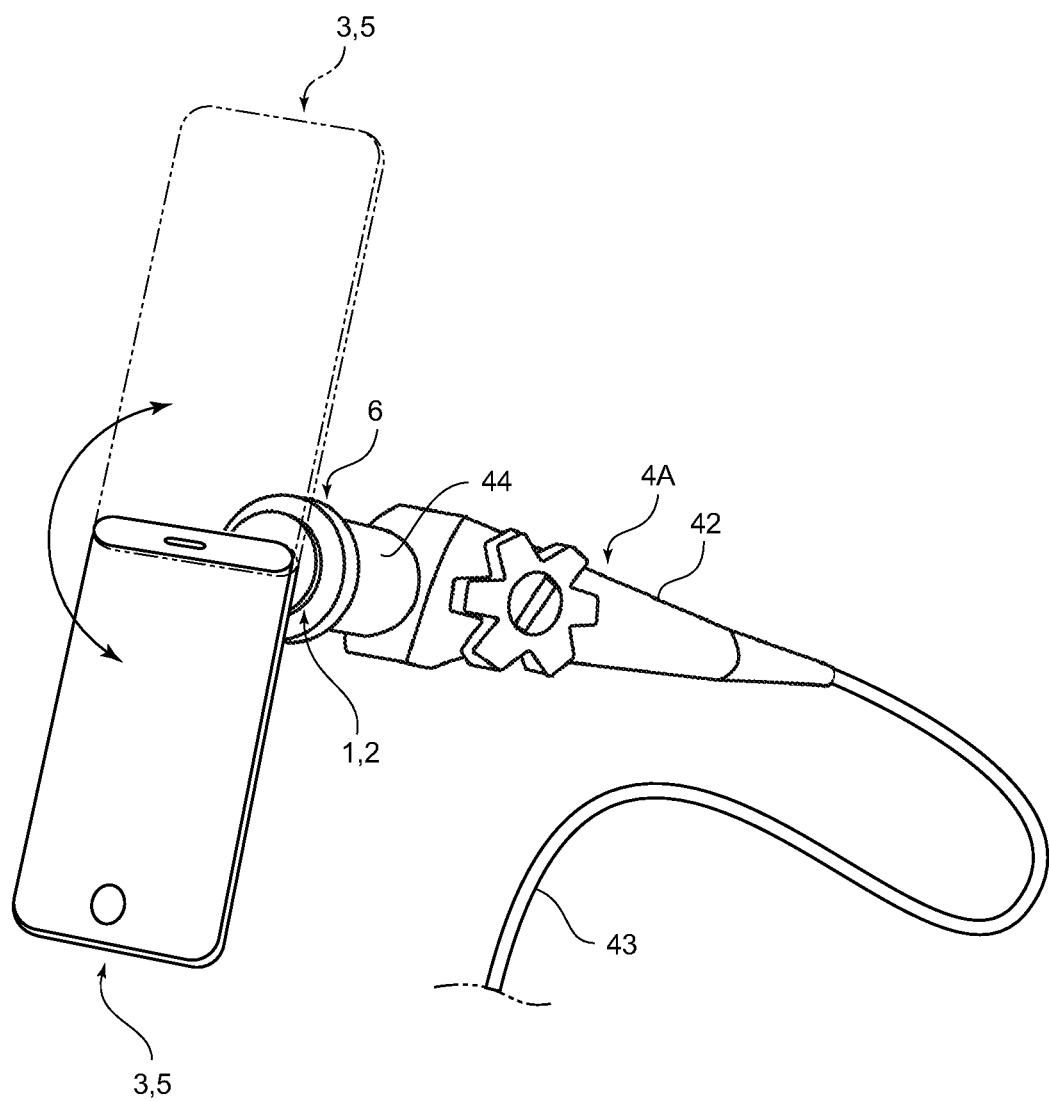
FIG. 19 is an explanatory diagram illustrating a fourth embodiment of the adaptor for attaching a camera-equipped mobile terminal according to the present invention (an explanatory diagram illustrating a used state in the case where the optical instrument is a fiberscope).

FIG. 19 is an explanatory diagram of a used state illustrating a fourth embodiment of the adaptor for attaching portable terminal according to the present invention. The adaptor according to the fourth embodiment is to be used in a case where an optical instrument being used is a fiberscope (an endoscope) 4A. In FIG. 19, components indicated by same reference signs as in FIGS. 1 to 18 indicate the same components as ones therein.

An optical instrument to be used with the adaptor according to the first, second or third embodiment is a microscope exemplified as the microscope 4. On the other hand, the optical instrument to be used with the adaptor according to the fourth embodiment is a fiberscope 4A. The fiberscope 4A includes an operation unit 42, an optical fiber portion 43 and an ocular lens unit 44. One end of the optical fiber portion 43 is connected to one end of the operation unit 42. The ocular lens unit 44 is provided at another end of the operation unit 42. A second adaptor part 2 is detachably attached to the ocular lens unit 44. A first adaptor part 1 on the side of a smartphone 3 is detachably attached to the second adaptor part 2.

The adaptor according to the fourth embodiment can achieve the effect substantially similar to the effect of the adaptor according to the first embodiment. That is, the adaptor according to the fourth embodiment can detachably attach the smartphone 3 to the fiberscope 4A via the first adaptor part 1 and the second adaptor part 2.

Examples Other than the Above Mentioned Embodiments

In each of the first, third and fourth embodiments, the smartphone 3 with a camera built-in is exemplified as a camera-equipped mobile terminal. In the present invention, however, it may be used a mobile terminal equipped with a camera function other than the smartphone 3 as a camera-equipped mobile terminal. In this case, a case attached to the mobile terminal equipped with the camera function is a case other than the case 5 of the first embodiment, specifically designed for the mobile terminal equipped with the camera function to be used.

In the first, second or fourth embodiment, the microscope 4 or the fiberscope (medical endoscope) 9 is exemplified as an optical instrument. In the present invention, however, it may be used as the optical instrument an optical instrument other than the microscope 4 and the fiberscope (medical endoscope) 9, for example, ophthalmic equipment such as a slit lamp or an optical instrument such as a telescope or binoculars.

In the first embodiment, the first adaptor part 1 is attached to the smartphone 3 via the fixing plate 7 and the case 5 which constitute a first attaching member provided separately from the smartphone 3. That is, the first embodiment is configured that the first adaptor part 1, the fixing plate 7, the case 5 and the smartphone 3 are each provided separately and that the first adaptor part 1 is fixed to the fixing plate 7, the fixing plate 7 is fixed to the case 5, and the case 5 is attached to the smartphone 3. In the scope of the present invention, however, it may be configured as that the first adaptor part 1 is formed integrally with the fixing plate 7, the fixing plate 7 is fixed to the case 5, and the case 5 is attached to the smartphone 3. Further, in the scope of the present invention, it may be configured as that the first adaptor part 1, the fixing plate 7 and the case 5 is formed integrally and that the case 5 is attached to the smartphone 3. In the scope of the present invention, it may be configured as that the first adaptor part 1 and the case 5 is formed integrally without using the fixing plate 7 and that the case 5 is attached to the smartphone 3. As described above, the adopter according to the scope of the present invention is to be configured as that the first adaptor part 1 is attached to the smartphone 3 via the first attaching member provided separately from the smartphone 3.

In the first embodiment, the first adaptor part 1 is attached to the smartphone 3 via the fixing plate 7 and the case 5 which constitute a first attaching member provided separately from the smartphone 3. In the scope of present invention, however, the first adaptor part 1 may be formed integrally with a casing or housing of the smartphone 3 without using the fixing plate 7 and the case 5 as the first attaching member. That is, in the scope of the present invention, the first adaptor part 1 may be provided integrally with the smartphone 3.

In the first and second embodiments, the second adaptor part 2 is attached to the microscope 4 via the optical member 6 or the member 6A constituting the second attaching member provided separately from the microscope 4. In the scope of the present invention, however, the second adaptor part 2 may be formed integrally with the barrel 40 and the ocular lens unit 41 of the microscope 4 without using the optical member 6 or the member 6A as the second attaching member. The second adaptor part 2 may also be attached directly to a C attach portion of a microscope with a trinocular tube or via the optical member 6 or the member 6A provided separately from the microscope with the trinocular tube. The second adaptor part 2 may also be attached not to the C attach portion but to an imaging barrel of the microscope with the trinocular tube directly or via the optical member 6 or the member 6A provided separately from the microscope with the trinocular tube.

Each of the first to fourth embodiments comprises the first lock portion 12 and the second lock portion 22. In the scope of the present invention, however, the first lock portion 12 and the second lock portion 22 are not to be necessarily provided. In such a case, the first adaptor part 1 and the second adaptor part 2 can stand still at a predetermined position by means of gravity on the first adaptor part 1 and also the smartphone 3 with the first stopper portion 11 and the second stopper portion 21 being in contact with each other. Such a configuration makes the lock structure unnecessary and the structure of the adopter simple to reduce a manufacturing cost. Moreover, in such a configuration, the smartphone 3 does not drop by gravity unless the smartphone 3 indicated with a solid line in FIG. 16 is rotated 90° or more. In this manner, imaging can be performed while holding the smartphone 3 at a horizontal position with a simple structure.

Note that the present invention is not to be limited to the exemplified embodiments. In the scope of the present invention, the structure of the first slide portions 10, the first stopper portion 11 and the first lock portion 12 of the first adaptors part 1 and 1A may be replaced by the structure of the second slide portions 20, the second stopper portion 21 and the second lock portion 22 of the second adaptors part 2 and 2A while the structure of the second slide portions 20, the second stopper portion 21 and the second lock portion 22 of the second adaptors part 2 and 2A may be replaced by the structure of each of the first slide portions 10, the first stopper portion 11 and the first lock portion 12 of the first adaptors part 1 and 1A.

The invention claimed is:

1. An adaptor for attaching a camera-equipped mobile terminal on an optical instrument comprising: a first adaptor part for the camera-equipped mobile terminal and a second adaptor part for the optical instrument, the first adaptor part and the second adaptor part including: a first slide portion and a second slide portion detachably and slidably engaged to each other in a straight line direction; a first stopper portion and a second stopper portion coming into contact with each other to allow the first adaptor part and the second adaptor part to be stopped at a predetermined position; and a first lock portion and a second lock portion by which the first adaptor part and the second adaptor part are locked at a predetermined stop position when the first stopper portion and the second stopper portion come into contact with each other, the first adaptor part comprising a U-shaped portion, the first slide portion being provided on each of two straight arm portions of the U-shaped portion, the first stopper portion being provided on an arc-shaped closed part of the U-shaped portion, the first lock portion being provided on each end part of the arm portions of the U-shaped portion, having a projecting shape projecting inclinedly from the arm portion provided thereon, and being formed as elastically deformable for contacting with the second lock portion elastically, the second adaptor part comprising a tongue-shaped portion, the second slide portion being provided on each side of the tongue-shaped portion, the second stopper portion being provided on an arc-shaped part of the tongue-shaped portion, and the second lock portion being provided on an end of the second slide portion apart from the arc-shaped part inclinedly so as to match with the first lock portion.

2. The adaptor according to claim 1, wherein the first adaptor part and the second adaptor part are immobilized at a predetermined position where the first stopper portion and the second stopper portion are in contact with each other by means of gravity on the first adaptor part.

3. The adaptor according to claim 1, wherein
the first adaptor part is attached to a mobile terminal via a first attaching member provided separately from the mobile terminal or provided integrally with the mobile terminal, and
the second adaptor part is attached to the optical instrument via a second attaching member provided separately from the optical instrument or provided integrally with the optical instrument.

4. The adaptor according to claim 3, wherein the first attaching member is a case attached to the mobile terminal or a fixing tool fixed to the mobile terminal.

5. The adaptor according to claim 3, wherein the second attaching member is a member having an optical system and to be inserted into a barrel of the optical instrument, or a member fixed to an ocular lens or an object having a lens of the optical instrument.

* * * * *